US012605184B2

(12) United States Patent
Jennings et al.

(10) Patent No.: US 12,605,184 B2
(45) Date of Patent: Apr. 21, 2026

(54) TISSUE-REMOVING CATHETER WITH DISTAL TIP

(71) Applicant: MEDTRONIC VASCULAR INC., Santa Rosa, CA (US)

(72) Inventors: Eoghan Jennings, Summerhill (IE); Alan Ryan, Galway (IE); Tomas K. Kelly, Galway (IE); Michael James Donegan, Galway (IE)

(73) Assignee: MEDTRONIC VASCULAR, INC., Santa Rosa, CA (US)

( * ) Notice: Subject to any disclaimer, the term of this patent is extended or adjusted under 35 U.S.C. 154(b) by 951 days.

(21) Appl. No.: 17/812,546

(22) Filed: Jul. 14, 2022

(65) Prior Publication Data

US 2023/0063136 A1      Mar. 2, 2023

Related U.S. Application Data

(60) Provisional application No. 63/236,179, filed on Aug. 23, 2021.

(51) Int. Cl.
*A61B 17/3207* (2006.01)
*A61B 17/00* (2006.01)
(52) U.S. Cl.
CPC .............. *A61B 17/320758* (2013.01); *A61B 17/00234* (2013.01); *A61B 2017/00292* (2013.01); *A61B 2017/00845* (2013.01); *A61B 2017/00867* (2013.01); *A61B 2017/320733* (2013.01)
(58) Field of Classification Search
CPC ...... A61B 17/320758; A61B 17/00234; A61B 2017/00292; A61B 2017/00845; A61B 2017/00867; A61B 2017/320733; A61B 2017/00477; A61B 2017/22038
See application file for complete search history.

(56) References Cited

U.S. PATENT DOCUMENTS

| | | | |
|---|---|---|---|
| 6,428,552 | B1 | 8/2002 | Sparks |
| 9,750,509 | B2 | 9/2017 | Carrison |
| 10,405,879 | B2 | 9/2019 | WasDyke et al. |
| 10,786,278 | B2 | 9/2020 | Nishio et al. |
| 2002/0007190 | A1 | 1/2002 | Wulfman et al. |
| 2018/0317952 | A1 | 11/2018 | Jamous et al. |

(Continued)

FOREIGN PATENT DOCUMENTS

| WO | 2013123007 A1 | 8/2013 |
|---|---|---|

OTHER PUBLICATIONS

Extended European Search Report for corresponding application No. 22190256.2, Jan. 3, 2023, 10 pages, Munchen, Germany.

*Primary Examiner* — Ankit D Tejani
*Assistant Examiner* — Joshua Brendon Solomon
(74) *Attorney, Agent, or Firm* — Stinson LLP

(57)      ABSTRACT

A tissue-removing catheter for removing tissue in a body lumen includes an elongate drive member and a tissue-removing element operatively coupled to the distal end portion of the elongate drive member. An inner liner received within the drive coil defines a liner passage sized and shaped to receive a guidewire therein. A distal tip extends distally outward from the tissue-removing element. The distal tip has a proximal end portion disposed within the tissue-removing element and a distal end portion spaced distally from the tissue-removing element. A distal end portion of the inner liner is axially spaced apart from the proximal end portion of the distal tip such that the distal tip is free from direct connection to the inner liner.

20 Claims, 13 Drawing Sheets

(56) References Cited

U.S. PATENT DOCUMENTS

| | | |
|---|---|---|
| 2019/0247084 A1 | 8/2019 | Spangler et al. |
| 2019/0365412 A1 | 12/2019 | WasDyke et al. |
| 2020/0078038 A1 | 3/2020 | Fleming et al. |
| 2020/0155194 A1 | 5/2020 | Schneider et al. |
| 2020/0163693 A1 | 5/2020 | Nishio et al. |
| 2020/0337720 A1 | 10/2020 | Nishio et al. |

98

D5

100

D6

120'

TISSUE-REMOVING CATHETER WITH DISTAL TIP

CROSS-REFERENCE TO RELATED APPLICATION

The present application claims the benefit of U.S. Provisional Application No. 63/236,179, filed Aug. 23, 2021, the entirety of which is hereby incorporated by reference.

FIELD

The present disclosure generally relates to a tissue-removing catheter, and more particular, to a tissue-removing catheter including a distal tip.

BACKGROUND

Tissue-removing catheters are used to remove unwanted tissue in body lumens. As an example, atherectomy catheters are used to remove material from a blood vessel to open the blood vessel and improve blood flow through the vessel. This process can be used to prepare lesions within a patient's coronary artery to facilitate percutaneous coronary angioplasty (PTCA) or stent delivery in patients with severely calcified coronary artery lesions. Atherectomy catheters typically employ a rotating element which is used to abrade or otherwise break up the unwanted tissue.

SUMMARY

In one aspect, a tissue-removing catheter for removing tissue in a body lumen generally comprises an elongate drive member having an axis and proximal and distal end portions spaced apart from one another along the axis. The elongate drive member is sized and shaped to be received in the body lumen and configured to be rotated about the axis. A tissue-removing element is operatively coupled to the distal end portion of the elongate drive member. The tissue-removing assembly is configured to be rotated by the elongate drive member to remove the tissue in the body lumen. An inner liner is received within the drive coil and defines a liner passage sized and shaped to receive a guidewire therein. The inner liner has proximal and distal end portions. A distal tip extends distally outward from the tissue-removing element. The distal tip has a proximal end portion disposed within the tissue-removing element and a distal end portion spaced distally from the tissue-removing element. The distal tip defining a tip opening extending through the proximal and distal end portions. The tip opening is in communication with the liner passage and configured to receive the guidewire therein. The tissue-removing element is rotatable relative to the distal tip. The distal end portion of the inner liner is axially spaced apart from the proximal end portion of the distal tip such that the distal tip is free from direct connection to the inner liner.

In another aspect, a tissue-removing catheter for removing tissue in a body lumen generally comprises an elongate drive member having an axis and proximal and distal end portions spaced apart from one another along the axis. The elongate drive member is sized and shaped to be received in the body lumen and configured to be rotated about the axis. A tissue-removing element is operatively coupled to the distal end portion of the elongate drive member. The tissue-removing assembly is configured to be rotated by the elongate drive member to remove the tissue in the body lumen. An inner liner is received within the drive coil and defines a liner passage sized and shaped to receive a guidewire therein. The inner liner has proximal and distal end portions. A distal tip extends distally outward from the tissue-removing element. The distal tip has a proximal end portion disposed within the tissue-removing element and a distal end portion spaced distally from the tissue-removing element. The distal tip defining a tip opening extending through the proximal and distal end portions. The tip opening is in communication with the liner passage and configured to receive the guidewire therein. The tissue-removing element is rotatable relative to the distal tip. The bushing passage is in communication with the liner passage and the tip opening, and is configured to receive the guidewire therein. The distal end portion of the inner liner is fixedly coupled to the proximal end portion of the bushing. The distal tip is integrally formed with the bushing such that the distal tip and the bushing are formed as a one-piece structure.

BRIEF DESCRIPTION OF THE DRAWINGS

Corresponding reference characters indicate corresponding parts throughout the drawings.

DETAILED DESCRIPTION

Figure 1:
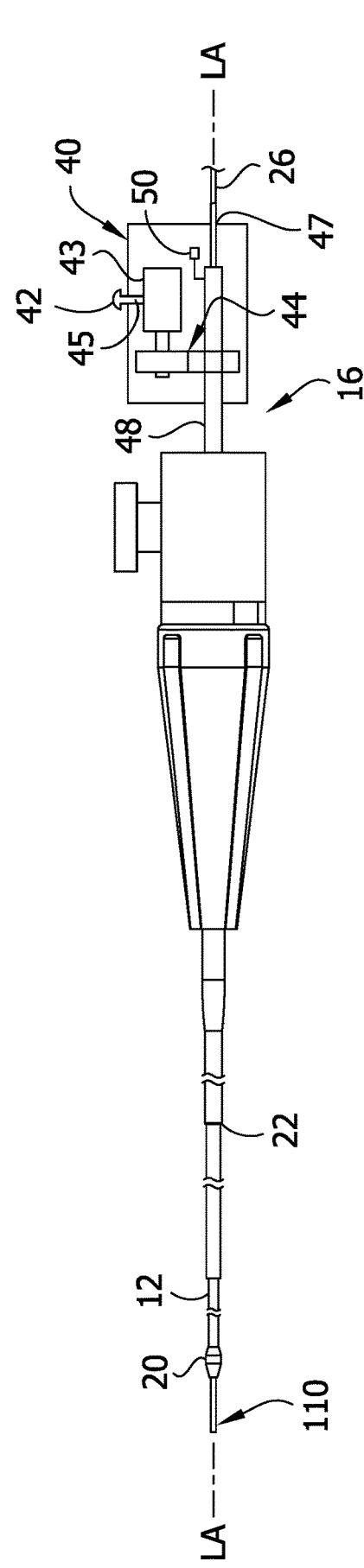
FIG. 1 is a schematic illustration of a catheter of the present disclosure.

Referring to the drawings, and in particular FIG. 1, a rotational tissue-removing catheter for removing tissue in a body lumen is generally indicated at reference number 10. The illustrated catheter 10 is a rotational atherectomy device suitable for removing (e.g., abrading, cutting, excising, ablating, etc.) occlusive tissue (e.g., embolic tissue, plaque tissue, atheroma, thrombolytic tissue, stenotic tissue, hyperplastic tissue, neoplastic tissue, etc.) from a vessel wall (e.g., coronary arterial wall, etc.). The catheter 10 may be used to facilitate percutaneous coronary angioplasty (PTCA) or the subsequent delivery of a stent. Features of the disclosed embodiments may also be suitable for treating chronic total occlusion (CTO) of blood vessels, and stenoses of other body lumens and other hyperplastic and neoplastic conditions in other body lumens, such as the ureter, the biliary duct, respiratory passages, the pancreatic duct, the lymphatic duct, and the like. Neoplastic cell growth will often occur as a result of a tumor surrounding and intruding into a body lumen. Removal of such material can thus be beneficial to maintain patency of the body lumen.

The catheter 10 is sized for being received in a blood vessel of a subject. Thus, the catheter 10 may have a maximum size of 3, 4, 5, 6, 7, 8, 9, 10, or 12 French (1, 1.3, 1.7, 2, 2.3, 2.7, 3, 3.3, or 4 mm) and may have a working length of 20, 30, 40, 60, 80, 100, 120, 150, 180 or 210 cm depending of the body lumen. While the remaining discussion is directed toward a catheter for removing tissue in blood vessels, it will be appreciated that the teachings of the present disclosure also apply to other types of tissue-removing catheters, including, but not limited to, catheters for penetrating and/or removing tissue from a variety of occlusive, stenotic, or hyperplastic material in a variety of body lumens.

Figure 2:
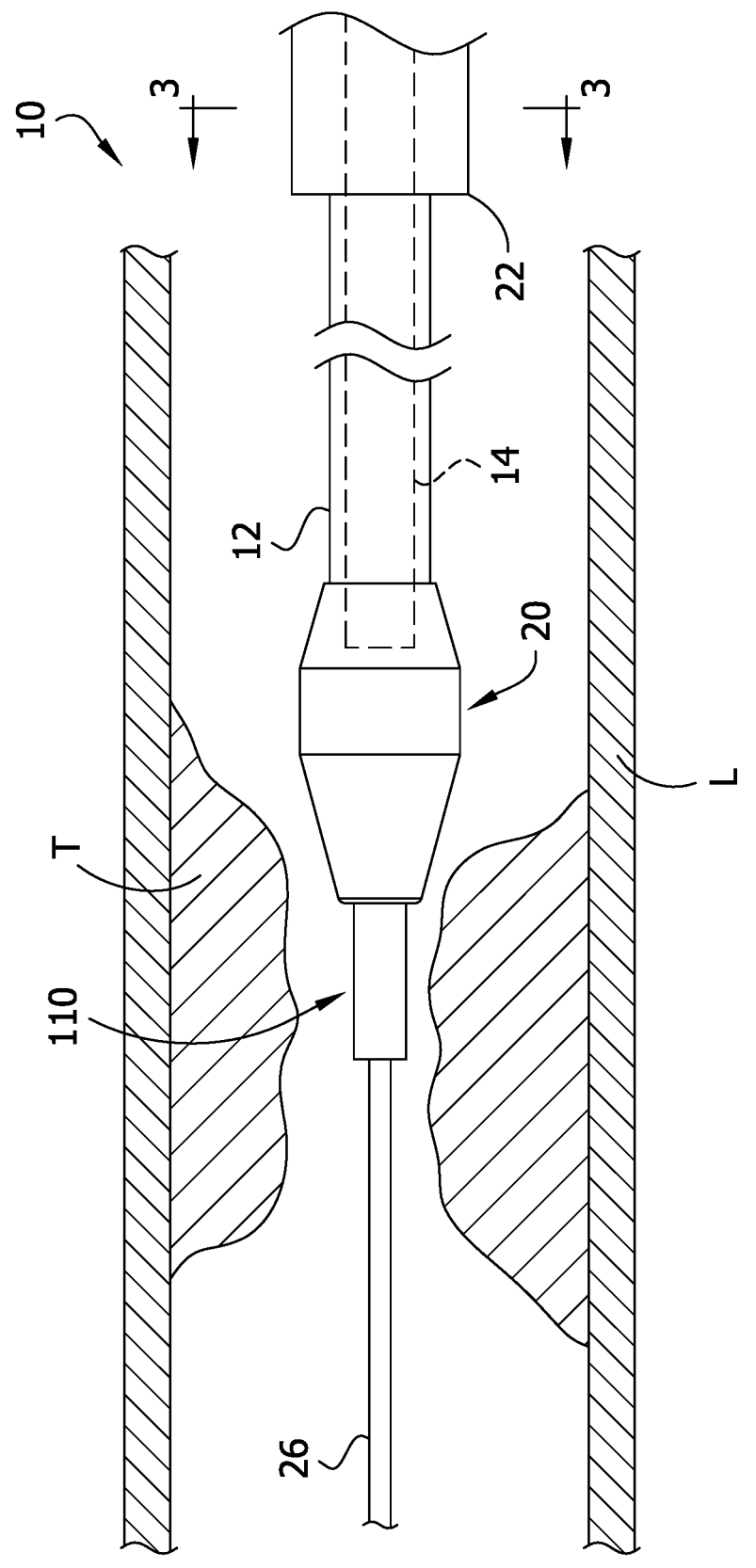
FIG. 2 is an enlarged elevation of a distal end portion of the catheter.
Figure 3:
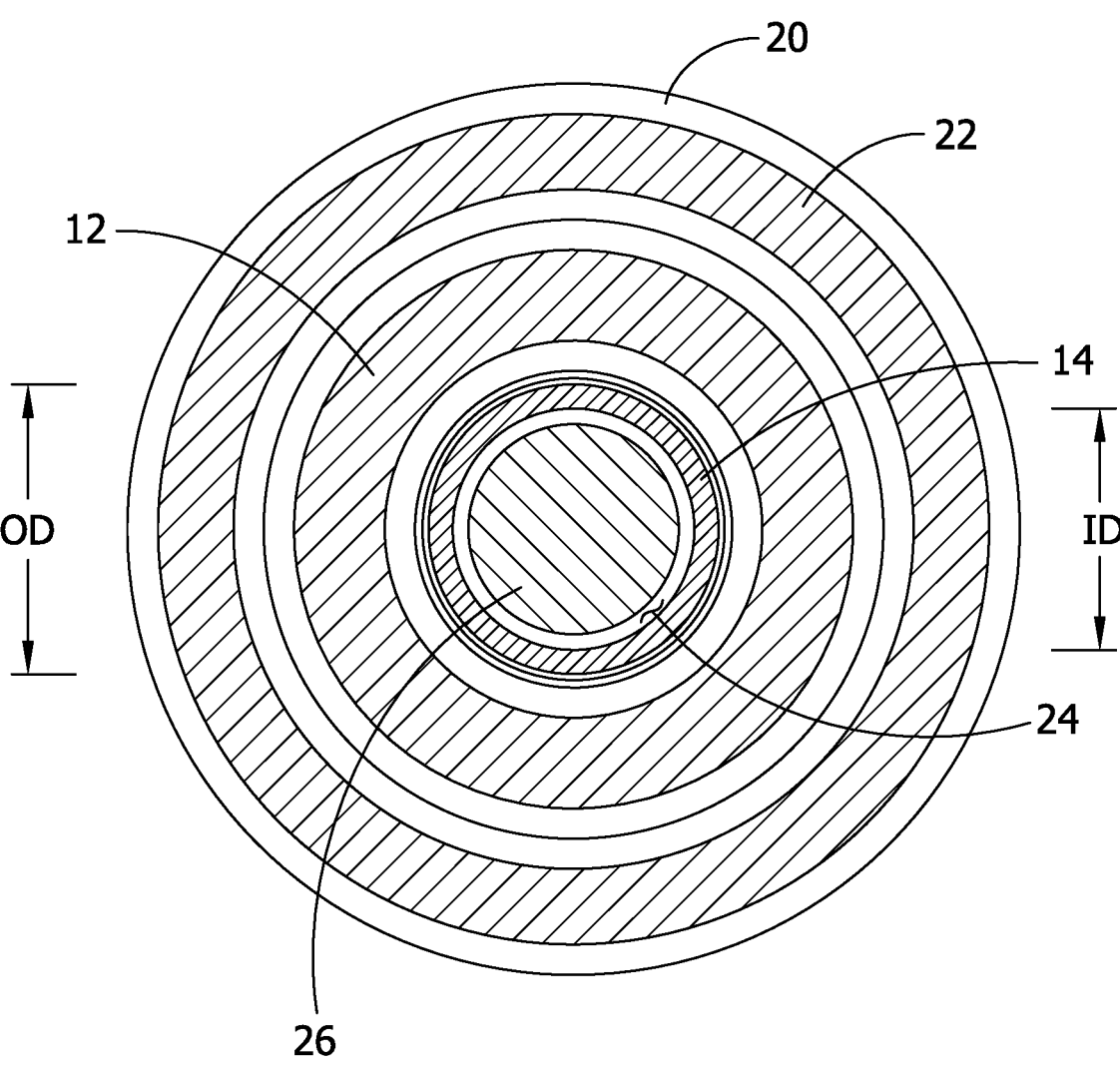
FIG. 3 is a cross section taken through line 3-3 in FIG. 2.

Referring to FIGS. 1-3, the catheter 10 comprises an elongate drive member, as illustrated a drive coil 12, disposed around an elongate inner liner 14 defining a liner passage 15. The elongate drive member may be another drive member other than the drive coil, such as a drive shaft, a drive lumen, or other type of elongate drive member. The drive coil 12 and inner liner 14 extend along a longitudinal axis LA of the catheter from a proximal end portion 16 to a distal end portion 18 of the catheter. A tissue-removing assembly 20 is disposed on a distal end of the drive coil 12 and is configured for rotation to remove tissue from a body lumen as will be explained in greater detail below. An isolation sheath 22 is disposed around the drive coil 12. The drive coil 12 and the inner liner 14 are both configured to translate relative to the isolation sheath 22. The catheter 10 is sized and shaped for insertion into a body lumen of a subject. The isolation sheath 22 isolates the body lumen from at least a portion of the drive coil 12 and inner liner 14. The inner liner 14 defines a guidewire lumen 24 (FIG. 3) for slidably receiving a guidewire 26 therein so that the catheter 10 can be advanced through the body lumen by traveling along the guidewire. The guidewire can be a standard 0.014-inch outer diameter, 300 cm length guidewire. In certain embodiments, the inner liner 14 may have a lubricious inner surface for sliding over the guidewire 26 (e.g., a lubricious surface may be provided by a lubricious polymer layer or a lubricious coating). In the illustrated embodiment, the guidewire lumen 24 extends along an entire working length of the catheter 10. In one embodiment, the overall working length of the catheter 10 may be between about 135 cm (53 inches) and about 142 cm (56 inches). In use, the guidewire 26 may extend by an extension distance, e.g. about 40 mm (1.6 inches), past a distal end of the inner liner 14.

Figure 4:
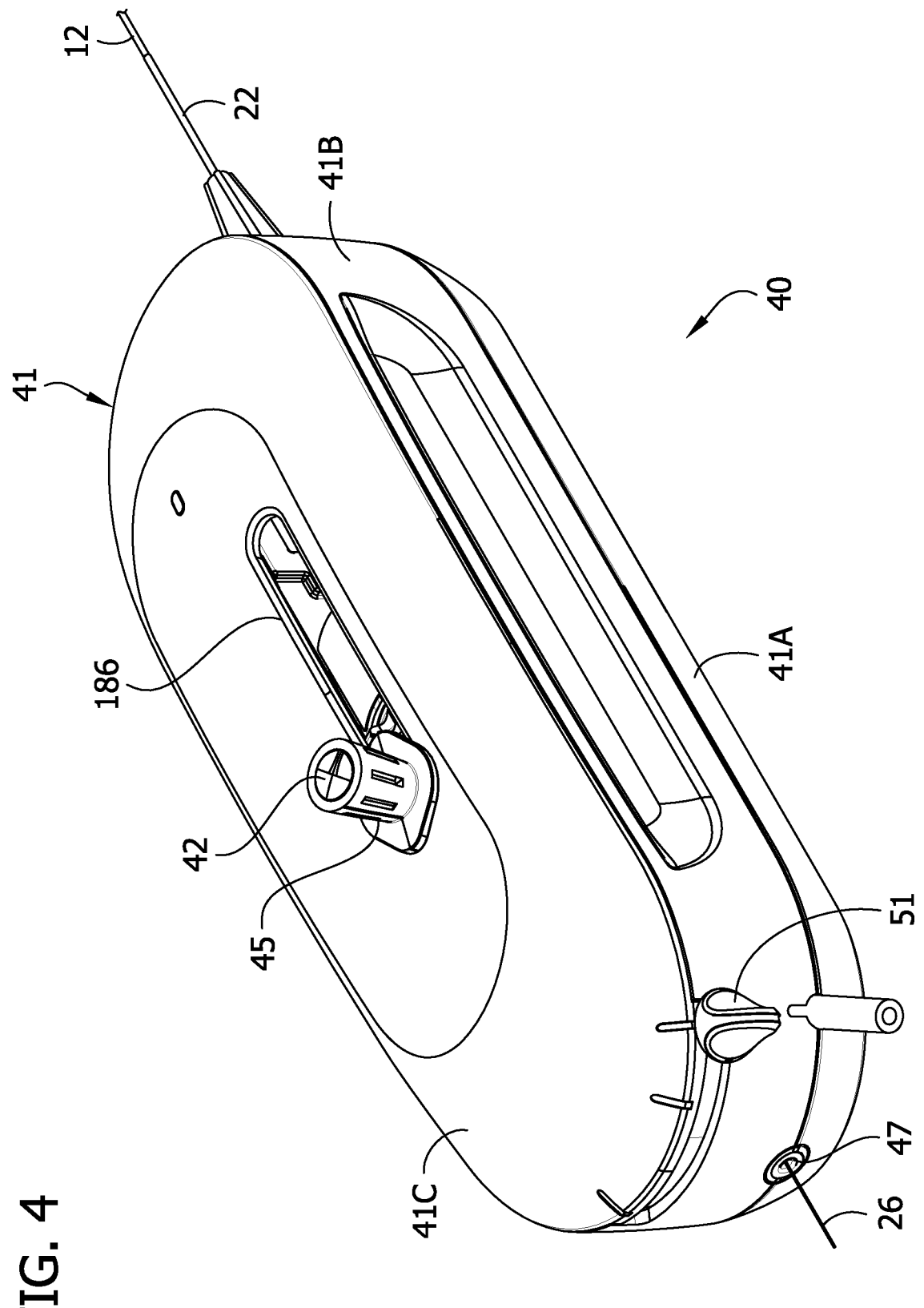
FIG. 4 is a perspective of a handle of the catheter.
Figure 5:
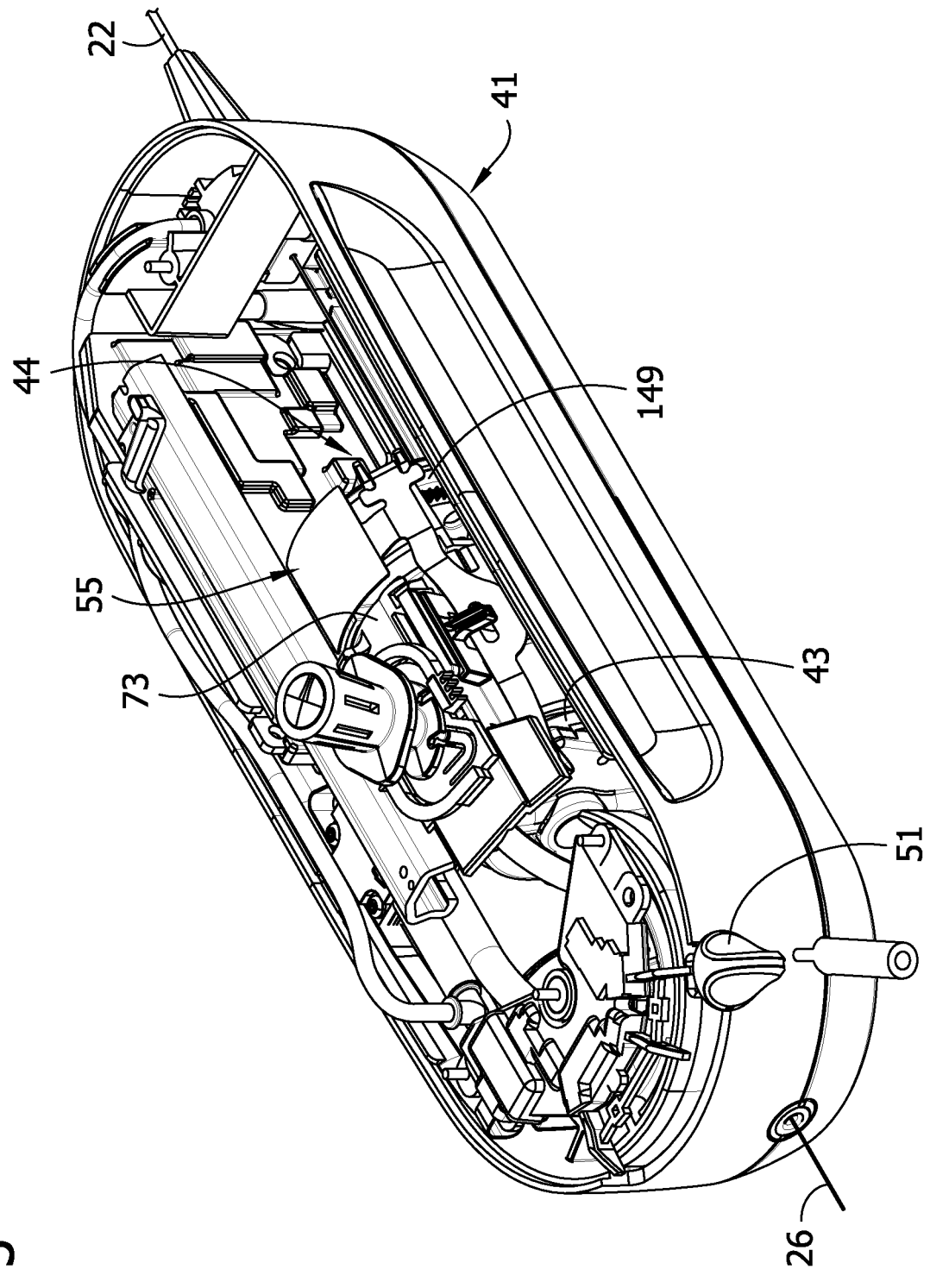
FIG. 5 is a perspective of the handle with a top housing section removed.

Referring to FIGS. 1, 4 and 5, the catheter 10 further comprises a handle 40 secured at a proximal end of the isolation sheath 22. As shown in FIGS. 4 and 5, the handle 40 comprises a housing 41 that supports the components of the handle. The housing 41 has a generally elongate egg shape and includes a plurality of housing sections secured together to enclose the internal components of the handle 40. In the illustrated embodiment, the housing 41 includes a bottom housing section 41A, a middle housing section 41B secured to the top of the bottom housing section, and a top housing section 41C secured to the top of the middle housing section. In one embodiment, the bottom housing section 41A is removable from the middle housing section 41B to provide access to the components of the handle 40 in the interior of the housing 41 by a user. It will be understood that the housing 41 can have other shapes and configurations without departing from the scope of the disclosure.

The housing 41 supports an actuator 42 (e.g., a lever, a button, a dial, a switch, or other device) configured for selectively actuating a motor 43 disposed in the handle to drive rotation of the drive coil 12, and the tissue-removing assembly 20 mounted on the distal end of the drive coil. The motor 43 is configured to rotate the drive coil 12 and tissue-removing assembly 20 at speeds of greater than about 80,000 RPM. In one embodiment, the motor 43 rotates the drive coil 12 and tissue-removing assembly 20 between about 10,000 and about 110,000 RPM.

Figure 6:
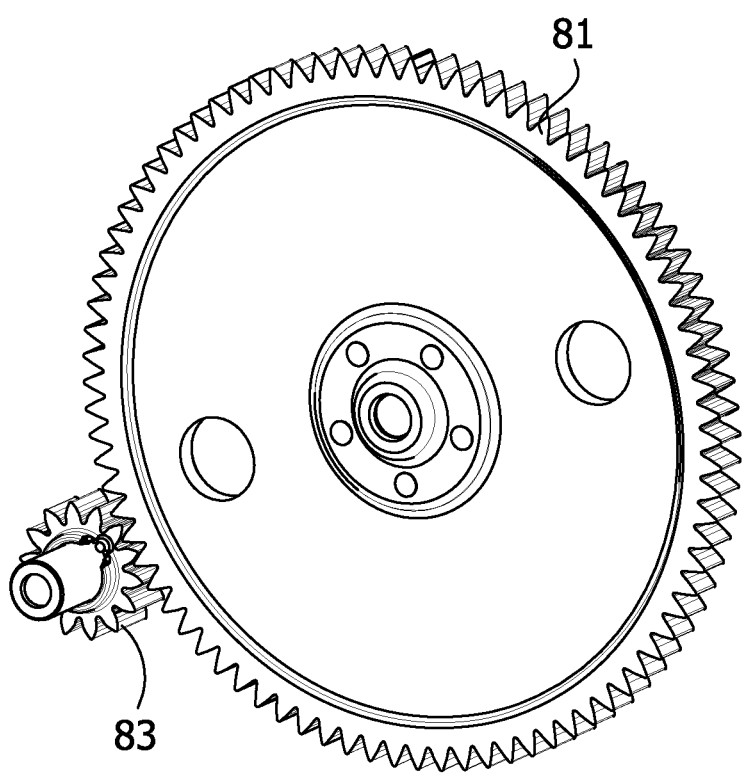
FIG. 6 is a perspective of gears of a gear assembly in the handle.

The motor 43 is coupled to the drive coil 12 by a gear assembly 44 and drive assembly 48 supported within the housing 41. As shown in FIG. 5, the gear assembly 44 comprises a gearbox housing 55 that mounts and at least partially encloses a pair of gears for transferring the rotation of a shaft of the motor 43 to the drive coil 12. The gearbox housing 55 also attaches to a carriage or advancer frame 73 for moving the motor 43 and gear assembly 44 within the housing 41. Further, attaching the gearbox housing 55 to the distal end of the advancer frame 73 secures the motor 43 in the advancer frame so that the motor moves along with the advancer frame. A driver gear 81 is attached to the motor 43 such that the driver gear rotates with the motor shaft when the motor 43 is activated (FIG. 6). A driven gear 83 is in mesh with the driver gear 81 so that rotation of the driver gear causes the driven gear to rotate in the opposite direction. The drive assembly 48 attaches the driven gear 83 to the drive coil 12 so that the rotation of the driven gear causes the drive coil to rotate. A controller 50 may be provided in the handle 40. The controller 50 may be programmed to control operation of the catheter.

It is understood that other suitable actuators, including but not limited to touchscreen actuators, wireless control actuators, automated actuators directed by a controller, etc., may be suitable to selectively actuate the motor in other embodiments. In some embodiments, a power supply may come from a battery (not shown) contained within the handle 40. The battery can provide the current source for the guidewire detection circuit. In other embodiments, the power supply may come from an external source.

Referring to FIGS. 1, 4, and 5, a slide or advancer 45 is positioned on the handle 40 and is operatively coupled to the inner liner 14 for movement of the inner liner relative to the handle to advance and retract the inner liner, drive coil 12, and tissue-removing assembly 20. The housing 41 of the handle 40 may define a slot 186 which limits the movement of the slide 45 relative to the handle. Thus, the length of the slot 186 determines the amount of relative movement between the inner liner 14 and the handle 40. In one embodiment, the slot has a length of about 70 mm (2.8 inches). The slide 45 is operatively attached to the advancer frame 73 so that movement of the slide causes movement of the advancer frame. The advancer frame 73 comprises an arch shaped body configured to slidingly receive the cylindrically shaped motor 43. In the illustrated embodiment, the actuator 42 is coupled to the advancer 45.

Referring to FIGS. 1 and 3, the isolation sheath 22 comprises a tubular sleeve configured to isolate and protect a subject's arterial tissue within a body lumen from the rotating drive coil 12. The isolation sheath 22 is fixed to the handle 40 at a proximal end of the sheath and does not rotate. The isolation sheath 22 provides a partial enclosure for the drive coil 12 and inner liner 14 to move within the sheath. The inner diameter of the isolation sheath 22 is sized to provide clearance for the drive coil 12. The space between the isolation sheath 22 and the drive coil 12 allows for the drive coil to rotate within the sheath and provides an area for saline perfusion between the sheath and drive coil. The outer diameter of the isolation sheath 22 is sized to provide clearance with an inner diameter of a guide catheter (not shown) for delivering the catheter 10 to the desired location in the body lumen. In one embodiment, the isolation sheath 22 has an inner diameter of about 0.050 inches (1.27 mm), an outer diameter of about 0.055 inches (1.4 mm), and a length of about 1500 mm (59 inches). The isolation sheath 22 can have other dimensions without departing from the scope of the disclosure. In one embodiment, the isolation sheath 22 is made from Polytetrafluorethylene (PTFE). Alternatively, the isolation sheath 22 may comprise a multi-layer construction. For example, the isolation sheath 22 may comprise an inner layer of perfluoroalkox (PFA), a middle braided wire layer, and an outer layer of Pebax.

Referring to FIGS. 1-3, the drive coil 12 may comprise a tubular stainless steel coil configured to transfer rotation and torque from the motor 43 to the tissue-removing assembly 20. Configuring the drive coil 12 as a coiled structure allows for the rotation and torque of the drive coil 12 to be applied to the tissue-removing assembly 20 when the catheter 10 is traversed across a curved path. The coil configuration of the drive coil 12 is also configured to expand its inner diameter when the coil is rotated so that the drive coil remains spaced from the inner liner 14 during operation of the catheter 10. In one embodiment, the drive coil 12 has an inner diameter of about 0.023 inches (0.6 mm) and an outer diameter of about 0.035 inches (0.9 mm). The drive coil 12 may have a single layer construction. For example, the drive coil may comprise a 7 filar (i.e., wire) coil with a lay angle of about 30 degrees. Alternatively, the drive coil 12 could be configured from multiple layers without departing from the scope of the disclosure. For example, the drive coil 12 may comprise a base coil layer and a jacket (e.g., Tecothane™) disposed over the base layer. In one embodiment, the drive coil comprises a 15 filar coil with a lay angle of about 45 degrees. The Tecothane™ jacket may be disposed over the coil. Alternatively, the drive coil 12 may comprise a dual coil layer configuration which also includes an additional jacket layer over the two coil layers. For example, the drive coil 12 may comprise an inner coil layer comprising a 15 filar coil with a lay angle of about 45 degrees, and an outer coil layer comprising a 19 filar coil with a lay angle of about 10 degrees. Drive coils having other configurations are also envisioned.

Referring to FIGS. 1-3 and 7, the illustrated inner liner 14 comprises a multiple layer tubular body configured to isolate the guidewire 26 from the drive coil 12 and tissue-removing assembly 20. The inner liner 14 is extendable through the handle 40 from a position within the handle to a position distal of the handle. In one embodiment, the inner liner 14 is coupled to the components within the handle 40 but is not fixedly attached to the housing 41 to allow translation of the inner liner relative to the housing. In another embodiment, the inner liner 14 is fixedly coupled to components within the handle 40 to prevent translation of the inner liner relative to the housing 41. The inner liner 14 has an inner diameter that is sized to pass the guidewire 26. The inner liner 14 protects the guidewire from being damaged by the rotation of the drive coil 12 by isolating the guidewire from the rotatable drive coil.

Figure 7:
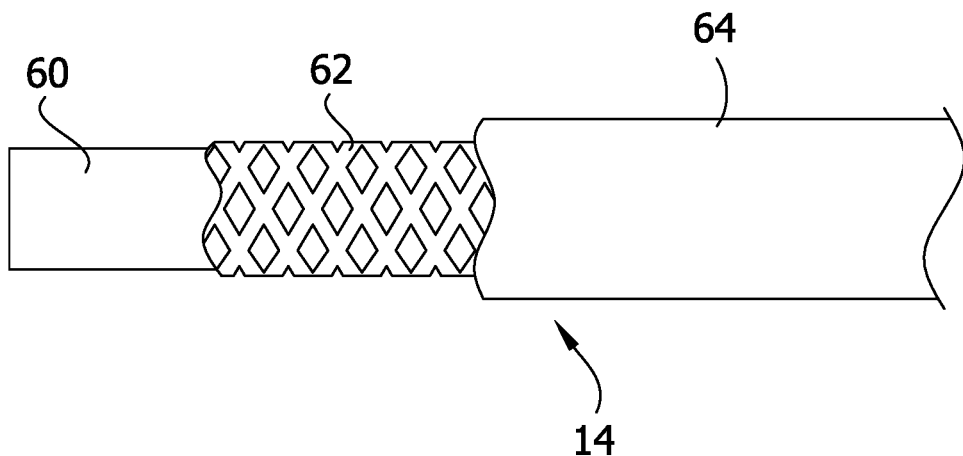
FIG. 7 is a fragmentary elevation of an isolation liner of the catheter with portions broken away to show internal details.

In the illustrated embodiment, as shown in FIG. 7, the inner liner 14 comprises an inner PTFE layer 60 an intermediate braided layer 62 comprised of stainless steel, and an outer layer 64 of polyimide (FIG. 7). The PTFE inner layer 60 provides the inner liner 14 with a lubricous interior which aids in the passing of the guidewire 26 though the inner liner. The braided stainless steel intermediate layer 62 provides rigidity and strength to the inner liner 14 so that the liner can withstand the torsional forces exerted on the inner liner by the drive coil 12. In one embodiment, the intermediate layer 62 is formed from 304 stainless steel. The outer polyimide layer 64 provides wear resistance as well as having a lubricous quality which reduces friction between the inner liner 14 and the drive coil 12. Additionally, a lubricious film, such as silicone, can be added to the inner liner 14 to reduce friction between the inner liner and the drive coil 12. In one embodiment, the inner layer 60, intermediate layer 62, and outer layer 64 extend along an entire length of the inner liner 14. Referring to FIG. 3, in one embodiment, the inner liner 14 has an inner diameter ID of about 0.016 inches (0.4 mm), an outer diameter OD of about 0.019 inches (0.5 mm), and a length of about 59 inches (1500 mm). The inner diameter ID of the inner liner 14 provides clearance for the standard 0.014-inch guidewire 26. The outer diameter OD of the inner liner 14 provides clearance for the drive coil 12 and tissue-removing assembly 20. The presence of a space between the inner liner 14 and the drive coil 12 reduces friction between the two components as well as allows for saline perfusion between the components.

Figure 8:
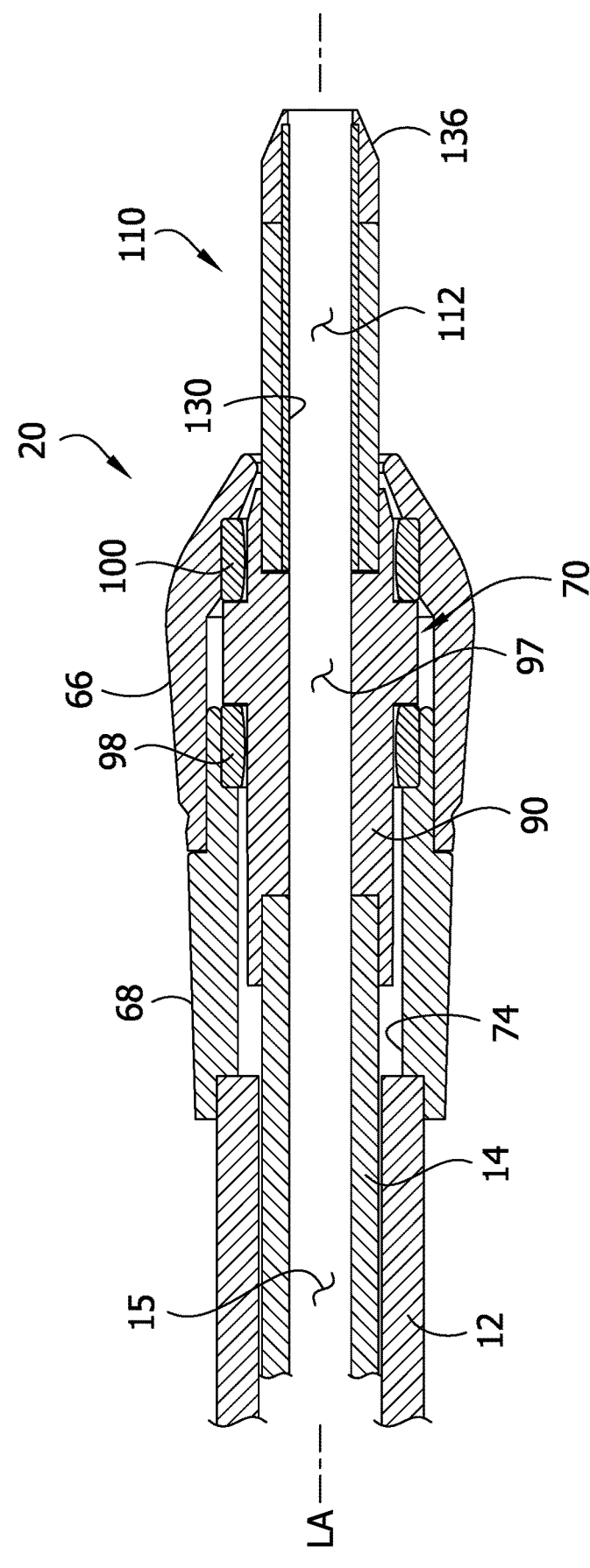
FIG. 8 is an enlarged fragmentary longitudinal cross section of the distal end portion of the catheter in FIG. 2.

Referring to FIGS. 1, 2, and 8, the tissue-removing assembly 20 extends along the longitudinal axis LA from a proximal end adjacent the distal end portion of the drive coil 12 to an opposite distal end. The tissue-removing assembly 20 is operatively connected to the motor 43 via the drive coil 12 for being rotated by the motor. When the catheter 10 is inserted into the body lumen and the motor 43 is rotating the tissue-removing assembly 20, the tissue-removing assembly is configured to remove occlusive tissue in the body lumen to separate the tissue from the wall of the body lumen.

Referring to FIG. 8, the illustrated tissue-removing assembly 20 includes a tissue-removing element 66 configured to engage and remove the tissue, a coupler 68 configured to operatively couple the tissue-removing element to the drive coil 12, and an internal bearing assembly, generally indicated at 70, configured to facilitate rotation of the tissue-removing element without damaging the inner liner 14.

Any suitable tissue-removing element 66 for removing tissue in the body lumen as it is rotated may be used in one or more embodiments. In the illustrated embodiment, the tissue-removing element 66 comprises an abrasive burr configured to abrade tissue in the body lumen when the motor 43 rotates the abrasive burr. The abrasive burr 66 has an abrasive outer surface formed, for example, by a diamond grit coating, surface etching, or the like. In other embodiments, the tissue-removing assembly can comprise one or more cutting elements having smooth or serrated cutting edges, a macerator, a thrombectomy wire, etc.

Referring still to FIG. 8, the coupler 68 has a proximal end fixedly secured to the drive coil 12, and a distal end fixedly secured to the proximal end of the tissue-removing element 66. The coupler transfers rotation from the drive coil 12 to the tissue-removing element 66. Together, the coupler 68 and the tissue-removing element 66 define an internal cavity 74 extending axially along the longitudinal axis LA. The coupler 68 may be formed from metal or other material, and may be welded and/or crimped to the drive coil and the tissue-removing element 66. The coupler 68 may be fixedly coupled to the drive coil 12 and the tissue-removing element 66 in other ways. In one or more embodiments, the tissue-removing assembly 20 may not include the coupler, but instead, the drive coil 12 may be fixedly coupled directly to the tissue-removing element 66, such as by welding or in other ways.

Figure 9:
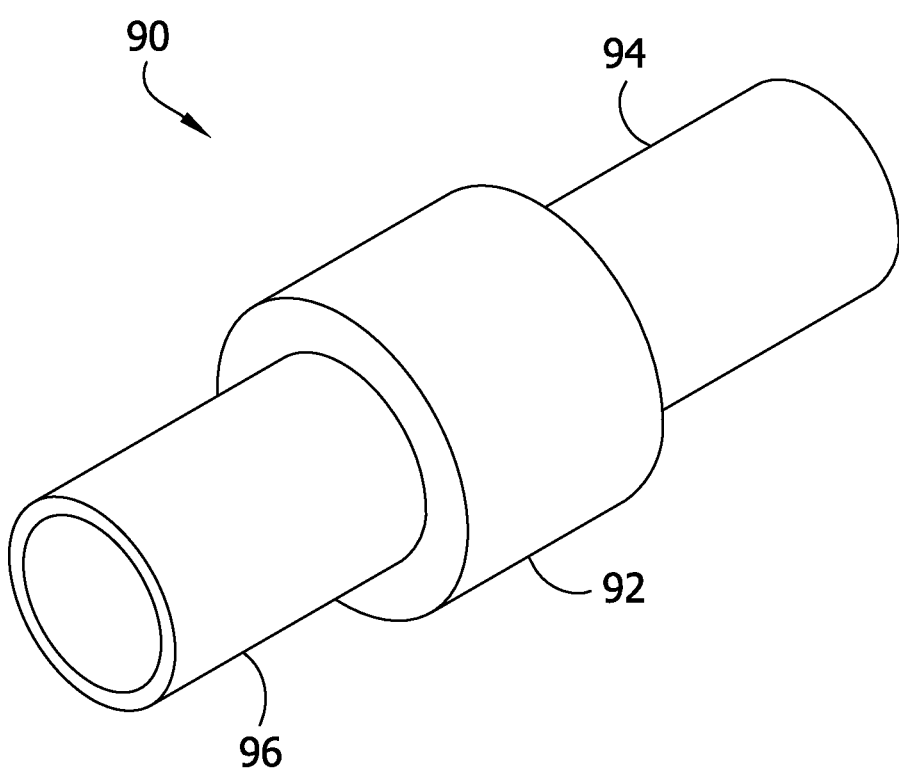
FIG. 9 is a perspective of a bushing of the catheter.
Figure 10:
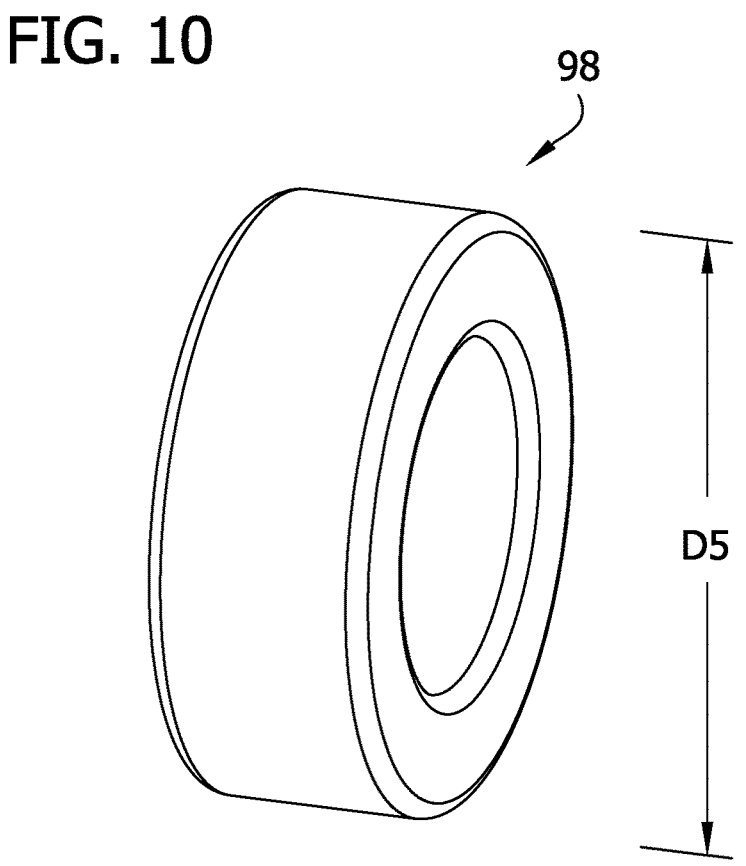
FIG. 10 is a perspective of a first bearing of the catheter.
Figure 11:
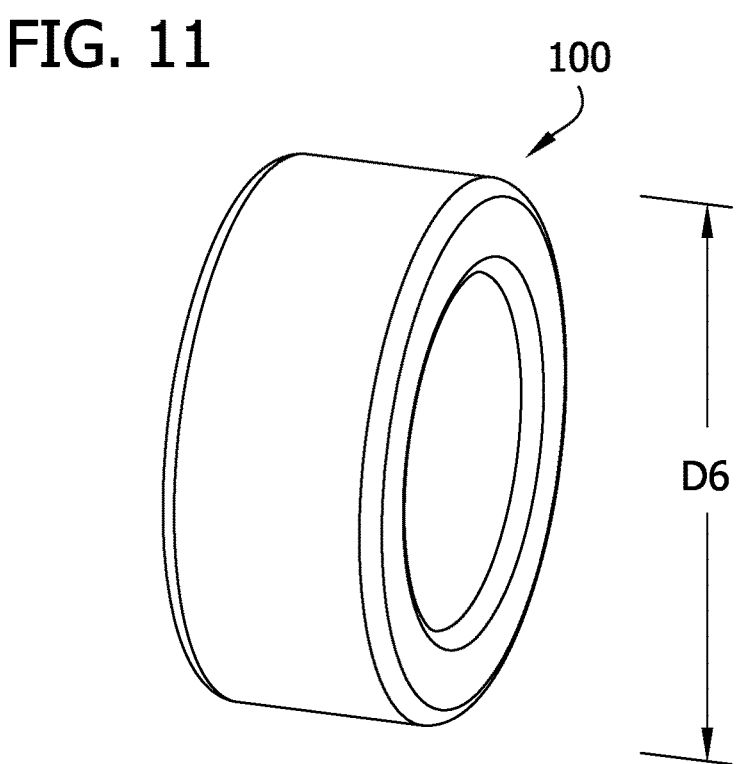
FIG. 11 is a perspective of a second bearing of the catheter.

Referring to FIGS. 8-10, the bearing assembly 70 includes a bushing 90 received in the internal cavity 74 of the tissue-removing assembly 20. As seen best in FIG. 9, the bushing 90 comprises a center ring portion 92, a proximal ring portion 94 extending proximally from the center ring portion, and a distal ring portion 96 extending distally from the center ring portion. The bushing 90 defines an axial passage 97 extending through the bushing. As shown in FIG. 8, a proximal counterbore at the proximal end of the internal passage of the bushing 90 receives a distal end of the inner liner 14. The inner liner 14 may be secured to the bushing within the proximal counterbore, such as by epoxy adhesive. In the illustrated embodiment, the center ring portion 92 has a larger outer diameter than the proximal and distal ring portions 94, 96. The center ring portion 92 is disposed in the second diameter portion 78 of the cavity 72, the proximal ring portion 94 is disposed in the first diameter portion 74, and the distal ring portion 96 is disposed in the second and third diameter portions 78, 82. In one embodiment, the bushing 90 is made from polyetheretherketone (PEEK) and polytetrafluoroethylene (PTFE). However, the bushing 90 can be formed from other material without departing from the scope of the disclosure.

Referring to FIGS. 8 and 10, a first bearing 98 is disposed around the proximal ring portion 94 of the bushing 90, and a second bearing 100 is disposed around the distal ring portion 96 of the bushing. The first bearing 98 has an outer diameter D5 that may be greater than an outer diameter D6 of the second bearing 100, although the diameters may be the same. In one embodiment, the bearings 98, 100 are made from Zirconia. The first bearing 98 is disposed in a counterbore of the cavity defined by the distal end coupler 68 and is held captive in the counterbore by a proximal end of the center ring portion 92 of the bushing 70. The second bearing 100 is disposed in a counterbore of the cavity adjacent a distal end of the tissue-removing element 66 and is held captive in the counterbore by a distal end of the center ring portion 92 of the bushing 70. As such the bushing 90 and bearings 98, 100 are held within the cavity of the tissue-removing assembly 20. Broadly, the bushing 90 and bearings 98, 100 may be considered a coupling assembly 57 for coupling the inner liner 14 to the tissue-removing assembly 20.

In the illustrated embodiment, rotation of the drive coil 12 and tissue-removing assembly 20 is not transmitted to the inner liner 14 such that the liner does not rotate with the drive coil 12. Rather the coupler 68, the tissue-removing element 66, and the bearings 98, 100 rotate about the bushing 90. And because the inner liner is fixedly attached to the bushing 90, which is retained within the cavity 74 of the tissue-removing assembly 20, the inner liner 14 is coupled to the drive coil and tissue-removing assembly through the bushing and bearing arrangement. Thus, the inner liner 14 will translate with the coil 12 and the tissue-removing assembly 20, however, the inner liner will not rotate with the drive coil and the tissue-removing element 66. It will be understood that the inner liner 14 may be coupled to the tissue-removing assembly 20 by other means. Alternatively, the inner liner 14 may not be coupled to the tissue-removing assembly 20.

Figures 12, 13:
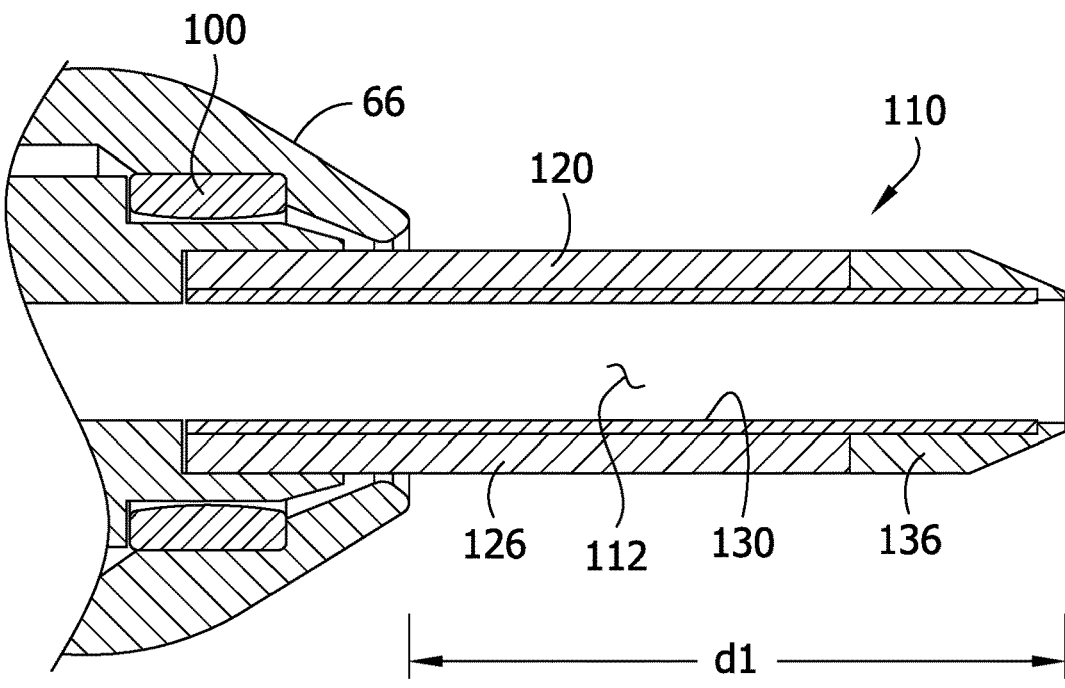
FIG. 12 is an enlarged view of a distal tip shown in FIG. 8.
FIG. 13 is a view of a frame of the distal tip.

Referring to FIGS. 8 and 12, the catheter 10 further includes a distal tip, generally indicated at 110, extending distally outward from the tissue-removing assembly 20. The illustrated distal tip 110 has a generally cylindrical shape with an axis extending along the longitudinal axis LA of the catheter 10. A proximal end of the tip 110 is fixedly coupled to the bushing 90 at a location within the tissue-removing assembly 20. In particular, the illustrated tip 110 is received in a distal counterbore of the bushing 90 adjacent the distal end of the bearing passage 70, and may be fixedly secured therein by adhesive or in other ways. The tip 110 may be fixedly coupled to the bushing 90 by thermal bonding or welding, heatshrink, adhesive, overmolding, or in other ways. The distal tip 110 extends through a distalmost opening defined by the tissue-removing element 66, and may project a distance d1 from about 0.5 mm to about 3.5 mm, or about 3 mm beyond the distalmost end of the tissue-removing element. The tip 110 defines a tip opening 112 extending axially through proximal and distal end thereof. The tip opening 112 is axially aligned and in communication with the bushing passage 97 and the liner passage 15. Together, the tip opening 112 and the passages 97, 15 are designed and constructed to receive a guidewire therein (e.g., a 0.014" guidewire). The diameters of the tip opening 112 and the passages 97, 15 may be equal or different, with the understanding that the sizes are suitable for receiving the guidewire therein. In one example, the diameters of the tip opening 112 and the passages 97, 15 are equal. The diameters may be from about 0.43 mm to about 0.50 mm, and in one example, about 0.44 mm. A maximum outer diameter of the tip 110 may be from about 0.55 mm to about 0.70 mm, and in one example about 0.63 mm.

Figure 14:
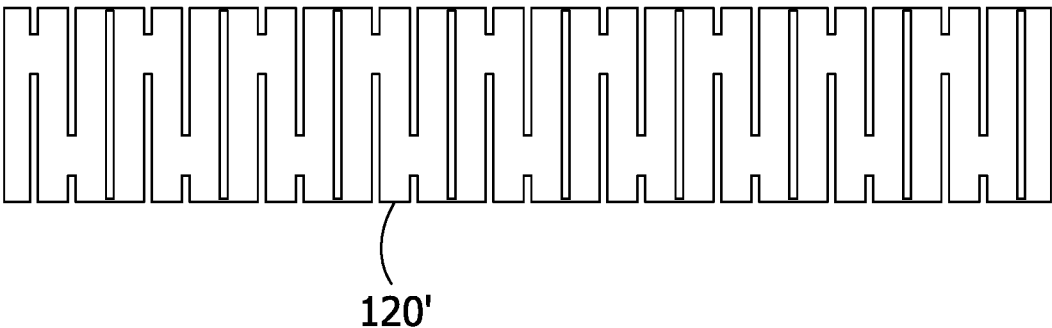
FIG. 14 is a view of another embodiment of the frame of the distal tip.

The tip 110 in general may be more flexible than the tissue-removing element 66 such that the tip facilitates centering of the tissue-removing element in the lesion to enhance effective deliver of the catheter into the lesion. The tip 110 may be less flexible than the guidewire to provide a suitable transition of stiffness between the guidewire and the tissue-removing element 66, which is believed to protect against guide damage. In one embodiment, shown in FIG. 12, the tip 110 may include a frame 120 to provide rigidity to the tip, while still allowing the tip to flex. In one example, the frame 120 may comprise (e.g., be formed from) a shape-memory material, such as Nitinol (nickel titanium). The frame 120 may be shape-set in a straight or linear configuration to resist bending, while allowing bending and enabling rebound to the linear configurations. The frame 120 may be braided from strands or filars of such material, as shown in FIG. 13. The stiffness of the frame 120 may be selected and achieved by a selecting a suitable filar density and/or suitable lay angle of the filars. In another example, as shown in FIG. 14, a frame 120' may be formed from a hypotube of the shape-memory material, such as Nitinol. The hypotube may be cut (e.g., laser cut) or otherwise formed with slots to adjust the stiffness of the frame 120'. The stiffness of the frame 120' may be selected and achieved by a suitable cut pattern for the slots and/or shapes and sizes of the slots.

The tip 110 may include a body layer 126 (e.g., an outer layer or encapsulating layer) including (e.g., formed from) a softer material that is softer and more flexible than the frame 120, 120'. For example, the body layer 126 may encapsulate (e.g., fully encapsulate) the frame 120, 120'. The material of the body layer 126 may have a Shore D hardness that is less than a Shore D hardness of the frame 120, 120'. As an example, the Shore D hardness of the material may be from about 55-72D. A suitable polymeric material may be a thermoplastic elastomer, a polyimide, or other materials. For example, the layer 126 may comprise block copolymers made up of rigid polyamide blocks and soft polyether blocks, among other thermoplastic elastomers. Together, the frame 120, 120' and the layer 126 encapsulating or overlying the frame may constitute the body of the tip 110. The layer 126 may be suitably adhered to the bushing 90.

Referring to FIG. 12, an inner layer 130 of the tip 110 may define at least a longitudinal portion of the tip opening 112. The inner layer 130 may define the inner surface of the tip 110. The inner layer 130, for example, may comprise a low friction material to reduce friction imparted on the guidewire 26, since the guidewire is immediately adjacent and may contact the inner layer. The inner layer 130 may comprise a polymeric material, such as polytetrafluoroethylene, perfluoroalkoxy, fluorinated ethylene propylene, and/or combination thereof. The inner layer 130 may extend along substantially the entire length of the tip 110, and may be spaced slightly from the distalmost end of the top.

Referring still to FIG. 12, the distal tip 110 may further comprise an atraumatic distalmost end portion 136. The distalmost end portion 136 is designed and constructed to inhibit damaging (e.g. perforating, dissecting, scraping, cutting, etc.) the body lumen (e.g., vessel) during delivery of the catheter 10 to the lesion. The distalmost end portion 136 may include a suitable material having a hardness that is less than the hardness of the body layer 126 and the frame 120, 120'. For example, the distalmost end portion 136 may comprise (e.g., be formed from) material have a Shore D hardness that is less than a Shore D hardness of the body layer 126 and the frame 120, 120'. As an example, the Shore D hardness of the material may be from about 55-72D. For example, the distalmost end portion 136 may comprise block copolymers made up of rigid polyamide blocks and soft polyether blocks, among other thermoplastic elastomers and polymers. In one example, the distalmost end portion 136 may be radiopaque to aid in fluoroscopic visualization. A filler material, such as tungsten or barium sulfate, may be included in the distalmost end portion 136. In the illustrated embodiment, the distalmost end of the distalmost end portion 136 is beveled to facilitate centering of the tissue-removing element 66 in the lesion.

Referring to FIG. 2, to remove tissue T in the body lumen L of a subject, a practitioner inserts the guidewire 26 into the body lumen L of the subject, to a location distal of the tissue T that is to be removed. Subsequently, the practitioner inserts the proximal end portion of the guidewire 26 through the guidewire lumen 24 of the inner liner 14 and through the handle 40 so that the guidewire extends through the proximal port 47 in the handle. With the catheter 10 loaded onto the guidewire 26, the practitioner advances the catheter along the guidewire until the tissue-removing assembly 20 is positioned proximal and adjacent the tissue T. When the tissue-removing assembly 20 is positioned proximal and adjacent the tissue T, the practitioner actuates the motor 43 using the actuator 42 to rotate the drive coil 12 and the tissue-removing assembly mounted on the drive coil. The tissue-removing assembly 20 abrades (or otherwise removes) the tissue T in the body lumen L as it rotates. While the tissue-removing assembly 20 is rotating, the practitioner may selectively move the drive coil 12 and inner liner 14 distally along the guidewire 26 to abrade the tissue T and, for example, increase the size of the passage through the body lumen L. The practitioner may also move the drive coil 12 and inner liner 14 proximally along the guidewire 26, and may repetitively move the components in distal and proximal directions to obtain a back-and-forth motion of the tissue-removing assembly 20 across the tissue T by sliding the advancer 45 back and forth within the slot 186 in the handle 40. During the abrading process, the inner liner 14 isolates the guidewire 26 from the rotating drive coil 12 and tissue-removing assembly 20 to protect the guidewire from being damaged by the rotating components. As such, the inner liner 14 is configured to withstand the torsional and frictional effects of the rotating drive coil 12 and tissue-removing assembly 20 without transferring those effects to the guidewire 26. When the practitioner is finished using the catheter 10, the catheter can be withdrawn from the body lumen L and unloaded from the guidewire 26 by sliding the catheter proximally along the guidewire. The guidewire 26 used for the abrading process may remain in the body lumen L for use in a subsequent procedure.

Figure 15:
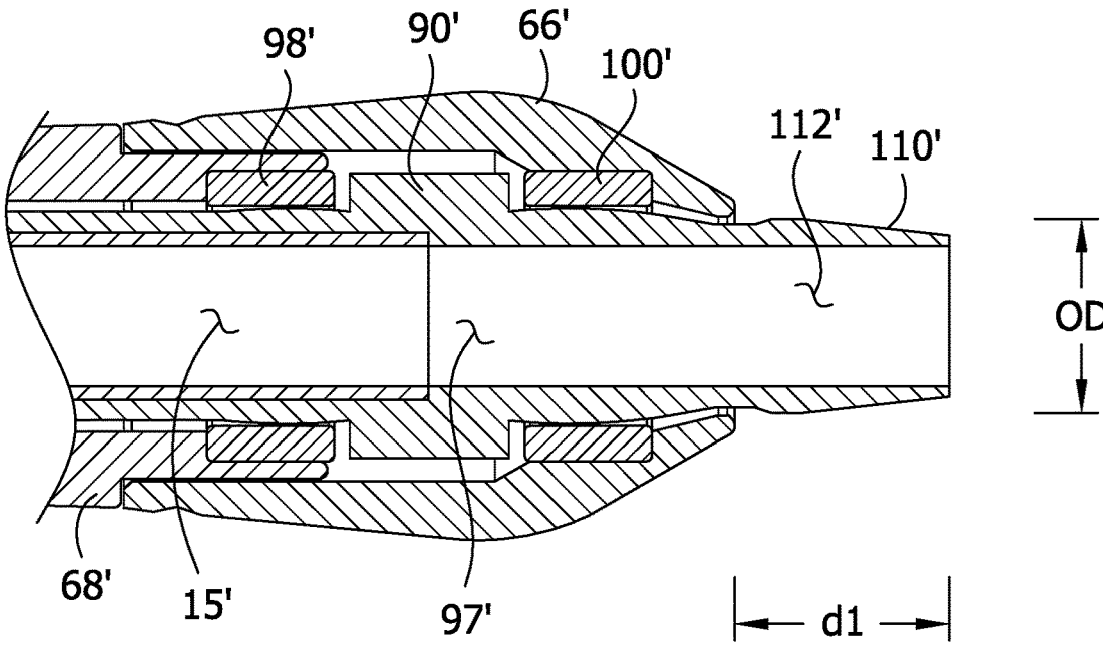
FIG. 15 is an enlarged fragmentary longitudinal cross section of a distal end portion of another embodiment of a catheter.
Figure 16:
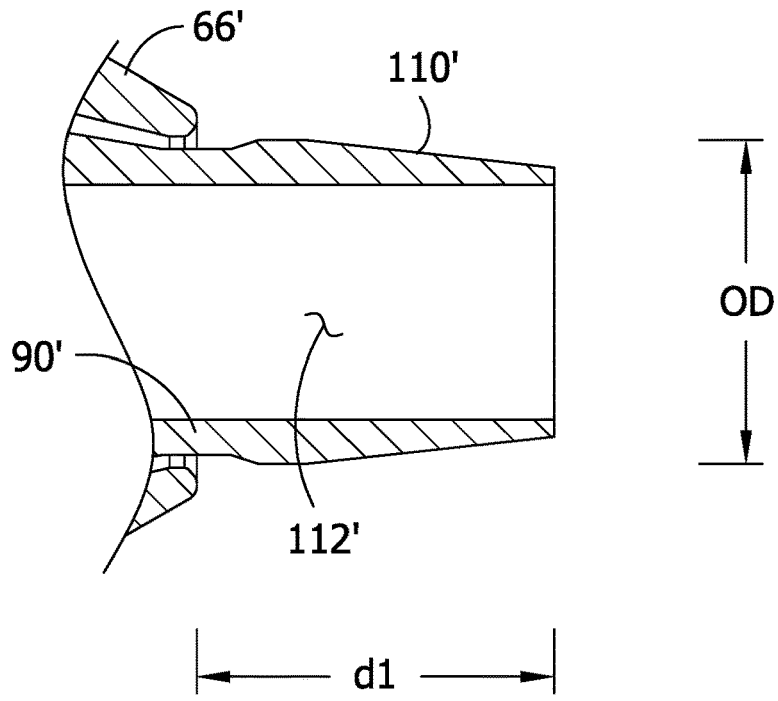
FIG. 16 is an enlarged view of a distal tip shown in FIG. 8.

Referring to FIGS. 15 and 16, another embodiment of a tissue-removing assembly for use with the catheter 10 is generally indicated at reference numeral 20'. This embodiment may be similar or identical to the tissue-removing assembly 20, except as described below herein. As an example, coupling 68', bearings 98, 100, and tissue-removing element 66 may be identical to the corresponding components of the first tissue-removing assembly 20. Unlike the first tissue-removing assembly, a distal tip 110' is integrally formed with a bushing 90' such that the distal tip and the bushing is an integrally formed, one-piece structure. In other words, a distal end portion of the bushing 90' defines the distal tip 110'. The other structures of the bushings 90' may be similar to identical to the structures of the first bushing 90.

The distal tip 110' extends through a distalmost opening defined by the tissue-removing element 66', and may project a distance d2 from about 2 mm to about 8 mm, or from about 2 mm to about 5 mm, or about 3 mm beyond the distalmost end of the tissue-removing element. The tip 110' defines a tip opening 112' extending axially through proximal and distal end thereof. The tip opening 112' is a continuation of (and axially aligned and in communication with) the bushing passage 97' and the inner liner passage 15'. Together, the tip opening 112' and the passages 97', 15' are designed and constructed to receive a guidewire therein (e.g., a 0.104" guidewire), as with the first embodiment. The diameters of the tip opening 112' and the passages 97', 15' may be equal or different, with the understanding that the sizes are suitable for receiving the guidewire therein. In one example, the diameters of the tip opening 112' and the passages 97', 15' are equal. The diameters may be from about 0.43 mm to about 0.50 mm, and in one example, about 0.44 mm. A maximum outer diameter of the tip 110 may be from about 0.55 mm to about 0.70 mm, and in one example about 0.63 mm.

The distal tip 110' in general may be more flexible than the bushing 90' and the tissue-removing element 66' such that the tip facilitates centering of the tissue-removing element in the lesion to enhance effective deliver of the catheter into the lesion. The tip 110' may be less flexible than the guidewire to provide a suitable transition of stiffness between the guidewire and the tissue-removing element 66', which is believed to protect against guide damage. The integrated tip 110' and bushing 90' also suitably isolates the guidewire 26 from the rotating tissue-removing element 66'. In one example, the tip 110' (and the bushing 90') may comprise one or more of PEEK (polyetheretherketone), Carbon fiber, and combinations thereof. For example, the integrated tip 110' and bushing 90' may be formed from a Carbon filled PEEK material, such as a 30% Carbon fiber reinforced PEEK material. The Carbon filled PEEK has a modulus of elasticity less than the modulus of elasticity of stainless steel. In the illustrated embodiment, the distal tip 110' has a wall thickness that is non-uniform along its length to promote flexing of the tip at the desired longitudinal location. In the illustrated embodiment, the tip 110' has a maximum wall thickness at its maximum outer diameter OD, which is adjacent to and spaced distally from the distalmost end of the tissue-removing element 66'. The wall thickness of the tip 110' decreases gradually (i.e., tapers) distally to decrease stiffness of the tip toward its distalmost end. The wall thickness of the tip 110' also tapers proximally toward the distal opening of the tissue-removing element 66'.

When introducing elements of the present invention or the one or more embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above apparatuses, systems, and methods without departing from the scope of the invention, it is intended that all matter contained in the above description and shown in the accompanying drawings shall be interpreted as illustrative and not in a limiting sense.

What is claimed is:

1. A tissue-removing catheter for removing tissue in a body lumen, the tissue-removing catheter comprising:
an elongate drive member having an axis and proximal and distal end portions spaced apart from one another along the axis, the elongate drive member being sized and shaped to be received in the body lumen and configured to be rotated about the axis;
a tissue-removing element operatively coupled to the distal end portion of the elongate drive member, the tissue-removing element being configured to be rotated by the elongate drive member to remove the tissue in the body lumen;
an inner liner received within a drive coil and defining a liner passage sized and shaped to receive a guidewire therein, the inner liner having proximal and distal end portions; and
a distal tip extending distally outward from the tissue-removing element, wherein the distal tip has a proximal end portion disposed within the tissue-removing element and a distal end portion spaced distally from the tissue-removing element, the distal tip defining a tip opening extending through the proximal and distal end portions of the distal tip, the tip opening being in communication with the liner passage and configured to receive the guidewire therein,
wherein the tissue-removing element is rotatable relative to the distal tip, and
wherein the distal end portion of the inner liner is axially spaced apart from the proximal end portion of the distal tip such that the distal tip is free from direct connection to the inner liner.

2. A tissue-removing catheter as set forth in claim 1, further comprising a bearing assembly operatively coupled to the tissue-removing element, wherein the inner liner and the distal tip are coupled to the bearing assembly.

3. A tissue-removing catheter as set forth in claim 2, wherein the bearing assembly includes a bushing having proximal and distal end portions and a bushing passage extending through the proximal and distal end portions, the distal end portion of the inner liner being fixedly coupled to the proximal end portion of the bushing, the proximal end portion of the distal tip being fixedly coupled to the distal end portion of the bushing, wherein the bushing passage is in communication with the liner passage and the tip opening, and is configured to receive the guidewire therein.

4. A tissue-removing catheter as set forth in claim 3, wherein the bearing assembly includes at least one bearing coupled to the tissue-removing element and engaging an exterior surface of the bushing.

5. A tissue-removing catheter as set forth in claim 1, wherein the distal tip includes a tip body that is more flexible than the tissue-removing element.

6. A tissue-removing catheter as set forth in claim 5, wherein the tip body includes a metal frame and a body layer encapsulating the metal frame.

7. A tissue-removing catheter as set forth in claim 6, wherein the metal frame includes a shape-memory metal.

8. A tissue-removing catheter as set forth in claim 6, wherein the body layer includes a polymeric material.

9. A tissue-removing catheter as set forth in claim 8, wherein the polymeric material is softer than material of the metal frame.

10. A tissue-removing catheter as set forth in claim 5, wherein the distal tip includes an inner layer inside the tip body and defining at least a longitudinal portion of the tip opening.

11. A tissue-removing catheter as set forth in claim 10, wherein the inner layer includes a low friction material to reduce friction imparted on the guidewire when the guidewire is received in the tip opening.

12. A tissue-removing catheter set forth in claim 5, wherein the distal tip includes an atraumatic distalmost end portion coupled to the tip body.

13. A tissue-removing catheter set forth in claim 12, wherein the atraumatic distalmost end portion includes a material having hardness less than the hardness of material of the tip body.

14. A tissue-removing catheter set forth in claim 13, wherein the atraumatic distalmost end portion includes a radiopaque material.

15. A tissue-removing catheter as set forth in claim 1, wherein the distal tip is more flexible than the bushing.

16. A tissue-removing catheter as set forth in claim 1, wherein the bushing and the distal tip each comprise one or more of PEEK (polyetheretherketone), Carbon fiber, and combinations thereof.

17. A tissue-removing catheter as set forth in claim 16, wherein the bushing and the distal tip each comprise Carbon fiber reinforced PEEK material.

18. A tissue-removing catheter as set forth in claim 16, wherein the distal tip has a wall thickness that is non-uniform to promote flexing of the distal tip.

19. A tissue-removing catheter for removing tissue in a body lumen, the tissue-removing catheter comprising:
an elongate drive member having an axis and proximal and distal end portions spaced apart from one another along the axis, the elongate drive member being sized and shaped to be received in the body lumen and configured to be rotated about the axis;
a tissue-removing element operatively coupled to the distal end portion of the elongate drive member, the tissue-removing element being configured to be rotated by the elongate drive member to remove the tissue in the body lumen;
an inner liner received within a drive coil and defining a liner passage sized and shaped to receive a guidewire therein, the inner liner having proximal and distal end portions;

a bushing having proximal and distal end portions and a
   bushing passage extending through the proximal and
   distal end portions; and
a distal tip extending distally outward from the tissue-
   removing element, wherein the distal tip has a proximal
   end portion disposed within the tissue-removing ele-
   ment and a distal end portion spaced distally from the
   tissue-removing element, the distal tip defining a tip
   opening extending through the proximal and distal end
   portions of the distal tip, the tip opening being in
   communication with the liner passage and configured
   to receive the guidewire therein,
wherein the tissue-removing element is rotatable relative
   to the distal tip,
wherein the bushing passage is in communication with the
   liner passage and the tip opening, and is configured to
   receive the guidewire therein,
wherein the distal end portion of the inner liner is fixedly
   coupled to the proximal end portion of the bushing, and
wherein the distal tip is integrally formed with the bush-
   ing such that the distal tip and the bushing are formed
   as a one-piece structure.

20. A tissue-removing catheter as set forth in claim 19,
wherein the distal end portion of the inner liner is axially
spaced apart from the proximal end portion of the distal tip
such that the distal tip is free from direct connection to the
inner liner.

\* \* \* \* \*